United States Patent
Kantham et al.

(10) Patent No.: US 6,743,952 B2
(45) Date of Patent: *Jun. 1, 2004

(54) SELECTIVE LIQUID PHASE AIR OXIDATION OF TOLUENE CATALYSED BY COMPOSITE CATALYTIC SYSTEM

(75) Inventors: Mannepalli Lakshmi Kantham, Andhra Pradesh (IN); Pentlavalli Sreekanth, Andhra Pradesh (IN); Kottapalli Koteshwara Rao, Andhra Pradesh (IN); Thella Prathap Kumar, Andhra Pradesh (IN); Bhavnari Purna C. Rao, Andhra Pradesh (IN); Boyapati Manoranjan Choudary, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/107,215

(22) Filed: Mar. 28, 2002

(65) Prior Publication Data

US 2003/0187304 A1 Oct. 2, 2003

(51) Int. Cl.$^7$ .......................... C07C 45/28; C07C 27/00; C07C 51/16

(52) U.S. Cl. .......................... 568/431; 568/815; 562/409
(58) Field of Search ................................ 568/431, 435, 568/815; 562/409

(56) References Cited

U.S. PATENT DOCUMENTS 6,495,726 B1 * 12/2002 Kantam et al.

FOREIGN PATENT DOCUMENTS

JP        2001 097913 A        4/2001

* cited by examiner

Primary Examiner—Johann Richter
Assistant Examiner—Sikarl A. Witherspoon
(74) Attorney, Agent, or Firm—Burns, Doane, Swecker & Mathis, L.L.P.

(57) ABSTRACT

The present invention provides an improved process for the production of benzaldehyde with 40–50% selectivity by the catalytic liquid phase air oxidation of toluene using a composite catalytic system comprising salts of iron, cobalt, manganese, molybdenum or nickel as recyclable catalyst, salts of manganese or copper as recyclable co-catalyst and cobalt bromide, sodium bromide, sodium chloride and zinc bromide as promoter.

15 Claims, 1 Drawing Sheet

Recyle Experiments

Figure 1:
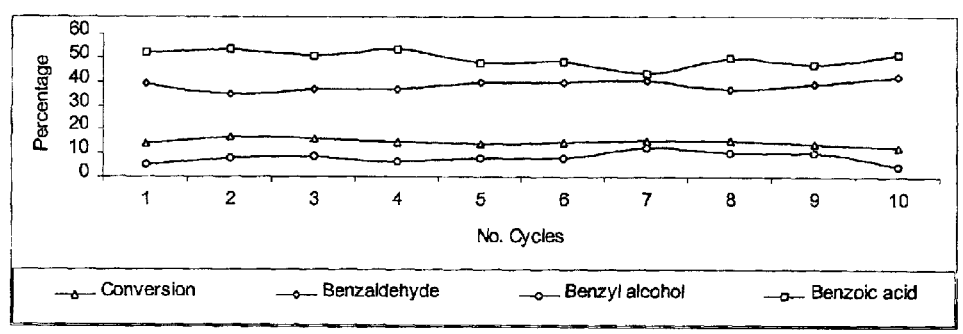

Reaction Volume: 200 ml; Toluene: 64.32 w/v% ; Cobalt acetate : 0.01 gmol/L; Manganese acetate : 0.0008 gmol/L; Sodium bromide : 0.0036gmol/L; Time : 1 h; Temperature : 120°C; Pressure : 10 bar; Air flow : 2 L/min.

- For each recycle, 5% of Cobalt acetate, 5% of Manganese acetate and 100% of Sodium bromide was added.

SELECTIVE LIQUID PHASE AIR OXIDATION OF TOLUENE CATALYSED BY COMPOSITE CATALYTIC SYSTEM

FIELD OF THE INVENTION

The present invention relates to a process for the production of benzaldehyde with 40–50% selectivity by catalytic liquid phase air oxidation of toluene using a composite catalytic system.

The N.F./F.C.C. grade of benzaldehyde is widely used in flavors such as almond and cherry and in various fragrances for soap and toiletries. Benzaldehyde is an F.D.A. sanctioned synthetic flavoring substance generally recognized as safe for food. The technical grade is a versatile chemical intermediate in the manufacture of pharmaceuticals, dyes, perfume and flavoring chemicals. The technical grade of benzoic acid is used as at intermediate in the manufacture of chemicals, alkyd resins, polyesters, plasticizers, dyestuffs, preservatives, and rubber activators and retardants. Benzoic acid, industrial grade, is used as a chemical intermediate and as a diverting agent in crude oil recovery applications.

BACKGROUND AND PRIOR ART OF THE INVENTION

Benzaldehyde is currently produced by the hydrolysis of the corresponding side chain halogenated toluene compound. Reference may be made to a patent U.S. Pat. No. 4,229,379, Oct. 21, 1980, wherein benzaldehyde is prepared by hydrolysis of benzyl chloride at 100–200° C. at normal or under increased pressures in the presence of an excessive aqueous hydrochloric acid. Reference may be made to another patent, U.S. Pat. No. 4,450,298, May 22, 1994, wherein vapour phase catalytic hydrolysis of benzylchloride to form benzaldehyde by using activated carbon treated with $H_2SO_4$ or impregnated with a metal chloride such as $FeCl_3$ or a metal sulphate such as cupric sulphate. The drawbacks in the above processes are generation of large excess of effluents and the benzaldehyde produced does not meet food grade specifications.

Air oxidation of toluene and its derivatives offers green technology path provided the desired selectivities are realised for market driven products and minimisation of halogenated and unwanted by-products causing effluents is achieved. Several patents have been filed describing innovation in air oxidation of toluene and its derivatives both in liquid and vapour phase.

One of the prevalent industrial practices for the vapour phase oxidation of toluene to benzaldehyde involves a uranium oxide/molybdenum oxide catalyst at 500–600° C. (W. L. Faith, D. B. Keyes and R. L. Clark, Industrial Chemicals, $3^{rd}$ Ed., John Wiley & Sons, Inc., New York, 1965; U.S. Pat. No. 3,579,589). Reference may be made to a patent, U.S. Pat. No. 3,946,067, wherein a process is described for the preparation of aromatic aldehydes such as benzaldehyde or substituted benzaldehydes involving the vapour phase oxidation of aralkyl compounds such as toluene or substituted toluenes, respectively, at temperatures of less than ~250° C. in the presence of a catalyst composition containing phosphoric acid and a catalytically effective amount of palladium metal. The aromatic aldehydes are produced in a single reaction step. The drawbacks in this process are the conversion of toluene has to be kept very low <4% to attain high selectivity (>70%) of benzaldehyde and significant amount of carbon dioxide is also formed in this process.

Reference may be made to another patent, U.S. Pat. No. 3,989,674, Nov. 2, 1976, wherein a mixture of toluene, oxygen and a helium diluent in molar ratio 1:2:8 is passed over the Cu— Au— silica catalyst at atmospheric pressure and temperatures in the range of 450–600° F. with 200–1000 volumes of gas/h/volume of catalyst. The selectivity of benzaldehyde is 75–80% at conversion levels 15–30%. Reference may be made to another patent, U.S. Pat. No. 4,137,259, Jan. 30, 1979, wherein a process for the vapour phase catalytic oxidation of toluene to benzaldehyde and benzoic acid at a temperature ranging from 300–500° C. in the presence of a silver-iron vanadate on silica with conversion 21%, selectivity to aldehyde 33% is described. Reference may be made to a patent U.S. Pat. No. 4,390,728, Jun. 28, 1983, wherein benzaldehyde is formed by the oxidation of toluene in the presence of a catalyst composed of the oxides of Cu, Fe, Pb, U, Mo, and P, which can also include some other promoter elements. The reaction conditions are 475–550° C., 0–10 atm. pressure, per pass conversion is 35–50%, selectivity to benzaldehyde 40–70%. Reference may be made to a publication by Ray et al, Ind. J. Technol., 21(4), 137, 1983, where they have reported a process for the oxidation of toluene to benzaldehyde. But, the conversion per pass is restricted to ~15% and the yield of benzaldehyde is generally not more than 70%, with $CO_2$ as main product. Further, the low concentration of toluene in the toluene-air feed mixture poses problems of recovery. The drawbacks in the above processes are the use of higher reaction temperatures, generation of carbon dioxide in large amounts contributing global warming. Therefore, these processes do not appear to be attractive.

Reference may be made to U.S. Pat. No. 5,476,827, Dec. 19, 1995, wherein aldehydes are prepared by the reduction of acids, esters in vapour phase in the presence of a bimetallic catalyst. The drawback is two-step process of oxidation of toluene, a desired raw material to benzoic acid and reduction of benzoic acid to benzaldehyde with hydrogen. Eventually, this process becomes uneconomical, when compared to a process of selective oxidation of toluene to benzaldehyde.

Reference may be made to a publication by Morimoto et al (J. Chem. Soc. Sect. B, 62, 1967), Fields et al (Adv. Chem. Ser., No. 76(2), 395) and Kamiya (Adv. Chem. Ser., No. 76(2), 193, 1968), they have reported that liquid phase air oxidation provides high yield of benzaldehyde when oxidation is carried out in acetic acid medium with cobalt acetate as catalyst and sodium bromide as promoter. The drawbacks are that this process suffers from the disadvantages of relatively low yield. Reference may be made to U.S. Pat. No. 2,959,613, wherein the liquid phase oxidation of toluene or its nucleus substituted materials of toluene such as xylene is carried out by oxygen under the presence of a catalyser containing a bromine compound and a heavy metallic compound (such as cobalt compound or manganese compound) along with a zinc compound or an alkaline earth metallic compound or an alkaline metallic compound. The drawbacks in this method are that the main product is the corresponding aromatic carbonic acid and either there is absolutely no production of the corresponding aromatic aldehyde or it is produced in a very small quantity as a by-product.

Reference may be made to Japanese patent No. SHO-53-5132, wherein in order to increase the selectivity of benzaldehyde or its nucleus substituted material, a large quantity of catalyser containing a cobalt compound and bromine compound is used. Reference may be made to another Japanese patent No. SHO-56-108728, Aug. 28, 1981, wherein the liquid phase air oxidation of toluene is carried out by a catalyst composing a heavy metallic compound, zinc and bromine compound at 30–180° C. and low pressure. The transformation percentage of toluene is maintained within a specific range with the advantage of the execution of the reaction employing carboxylic acid as solvent in the range 0.5–2.0 times with respect to toluene or its substituted material. By this method the selectivity of benzaldehyde is increased while formation of benzyl bromide is reduced to 2 mol %. However, the turn over number is 3–50 in these air oxidation reactions. The drawbacks in the above processes are low turn over numbers render the process uneconomical, the use of higher catalyst concentration hasten corrosion of reactors and excessive production of benzyl bromide is detrimental to the achieve desired quality of the product. Reference may be made to U.S. Pat. No. 3,969,405 wherein the oxidation of toluene in the presence of cobalt acetate, acid activator and molecular oxygen oxidant gives high yield of benzoic acid with selectivity to benzaldehyde 35%. Reference may be made to U.S. Pat. No. 5,473,101 wherein the oxidation of toluene is carried out in the presence of cobalt acetate, sodium bromide and hydrogen peroxide. Conversion is 90.6%, benzaldehyde 29.0% yield, benzoic acid, 55.6% yield. The drawbacks in the above processes are there is excessive production of benzyl bromide or its nucleus substituted material and therefore such a method cannot be said to be a satisfactory one from the point of view of industrial production.

Reference may be made to the Applicant's earlier European patent EP 1088810, (U.S. application Ser. No. 09/414, 473) wherein the oxidation of toluene carried out in the presence of cobalt acetate, manganese acetate and zinc bromide. Conversion is <25% with 35–40% benzaldehyde and 50–55% benzoic acid selectivities.

Reference may be made to a publication K. Bahranowski et.al. (Appl. Clay Science, 18, 2001, 1993) wherein Layered double hydroxides (LDHs) are used for oxidation of aromatic hydrocarbons with hydrogen peroxide as an oxidant. Reference may be made to a publication M. W. de Lange et.al. (Appl. Catal. A, 220, 2001, 41) wherein a divergent approach, deoxygenation of benzoic acid to benzaldehyde is reported recently using molecular hydrogen. These processes are uneconomical due to the use of expensive hydrogen peroxide and molecular hydrogen.

Obviously different approaches have been employed both at laboratory and commercial scale to prepare benzaldehyde and the traditional process has the disadvantage of forming unwanted and corrosive halogenated by-products. Thus, there still exist a need for an improved process for preparing benzaldehyde with high selectivity.

OBJECT OF THE PRESENT INVENTION

The main object of the present invention is to provide an improved process for the production of benzaldehyde with 40–50% selectivity by the catalytic liquid phase air oxidation of toluene using a composite catalytic system, which obviates the drawbacks as detailed above.

Another object of the present invention is to maintain transformation percentage <25% in the catalytic liquid phase air oxidation of toluene.

Still another object of the present invention is to use homogeneous metal salts comprising Co, Fe, Mn, Mo, Cu as catalysts and cobalt bromide, sodium bromide, zinc bromide, sodium chloride as promoters and bromine and chlorine sources in very low concentrations.

Yet another object of the present invention is to use sodium bromide and sodium chloride as promoter at lower ratios to achieve higher selectivity.

One more object of the present invention is to recycle the catalyst containing Co, Mn salts for 10 cycles with almost consistent activity and selectivity.

One another object of the present invention is to provide a process for the production of benzaldehyde (40–50%) using very low concentration of catalyst thereby rendering the process economical.

Another object of the present invention is to provide a process for the production of benzyl alcohol (5–10%), another value added product of toluene, along with the production of benzaldehyde using very low concentration of catalyst thereby rendering the process economical.

Yet another object of the present invention is to provide a process for preparing benzaldehyde at lower reaction temperatures normally in the range of 60–130° C.

Still another object of the present invention is to terminate the reaction to obtain high selectivity of benzaldehyde.

A further object of the present invention is to eliminate the formation of benzyl bromide which is detrimental to the quality of benzaldehyde.

SUMMARY OF THE INVENTION

The present invention provides an improved process for the production of benzaldehyde with 40–50% selectivity by the catalytic liquid phase air oxidation of toluene using a composite catalytic system comprising salts of iron, cobalt, manganese, molybdenum or nickel as recyclable catalyst, salts of manganese or copper as recyclable co-catalyst and cobalt bromide, sodium bromide, sodium chloride and zinc bromide as promoter.

DETAILED DESCRIPTION OF THE PRESENT INVENTION

Accordingly, the present invention provides an improved process for preparing benzaldehyde with 40–50% selectivity and transformation % <25% by catalytic liquid phase oxidation of toluene by using a composite catalytic system along with production of value added products benzyl alcohol (5–10%) and benzoic acid without any trace amounts of benzyl bromide, said process comprising: catalytic liquid phase air oxidation of toluene with continuous flow of air employing significantly reduced quantities of salts of Iron, Cobalt, Manganese, Molybdenum or Nickel as recyclable catalysts, manganese or copper salts as recyclable co-catalysts and cobalt bromide, sodium bromide, sodium chloride and zinc bromide as promoters in presence of a bromine source and 0.05 to 0.4% by wt. of a carboxylic acid at a temperature of 60–130° C. and a it pressure of 1–10 bar for a period of 0.5–1.5 hrs.

In an embodiment of the present invention, the conversion is restricted to 15–25%.

In another embodiment of the present invention, the selectivity to benzaldehyde is 40–50%.

In still another embodiment of the present invention, the selectivity to benzyl alcohol is 5–10%.

In yet another embodiment of the present invention, the carboxylic acid is selected from acetic acid, propionic acid and benzoic acids.

In a further embodiment of the present invention, the carboxylic acid is acetic acid.

In one more embodiment of the present invention, air is used as the oxidant.

In one another embodiment of the present invention, the temperature is kept in the range from 60–130° C.

In an embodiment of the present invention, the pressure is kept in the range of 1–10 bar.

In another embodiment of the present invention, the residence time is 0.5 to 1.5 hrs.

In still another embodiment of the present invention, the catalyst contains a heavy metallic compound such as cobalt, molybdenum or iron as catalyst.

In yet another embodiment of the present invention, the concentration of the heavy metallic catalytic salts with respect to toluene in the reaction system is in the range of 0.01–0.027 gmol/L.

In a further embodiment of the present invention, the co-catalyst contains a heavy metallic compound such as manganese or copper and their concentration with respect to toluene is in the range of 0.001–0.002 g mol/L.

In one more embodiment of the present invention, the catalyst and co-catalyst are organic acid salts such as formic acid salts, acetic acid salts and propionic acid salts of the heavy metallic compound.

In one another embodiment of the present invention, the promoter is a bromine compound such as cobalt, sodium or zinc bromide.

In an embodiment of the present invention, the concentration of the promoter in the reaction system with respect to the toluene is in the range of 0.001–0.215 gmol/L.

In another embodiment of the present invention, the admix of $Cl^-$ to $Br^-$ ions available from the co-catalyst enhances the rate of air oxidation of toluene and ensures the product mix devoid of benzyl bromide.

In still another embodiment of the present invention, recycle reactions conducted with the recovered catalyst near identical conversions and selectivities were obtained with addition of promoter or bromide on each recycle.

In yet another embodiment of the present invention, low concentration of catalyst, co-catalyst and promoter slows down corrosion on the reactor which is a very important factor affecting economics of the project.

In a further embodiment of the present invention, the catalyst and co-catalyst are recycled for 10 cycles, which shows almost consistent activity and selectivity.

In one more embodiment of the present invention, the turn over number is in the range of 900–1200.

In one another embodiment of the present invention, the process totally eliminates the formation of benzyl bromide as a by-product.

In an embodiment of the present invention, the benzaldehyde produced is chlorine free and can be used for a wide range of applications.

In another embodiment of the present invention, the process is environmentally safe since there is no effluent disposal problem.

In still another embodiment of the present invention, the process is economical.

An improved process for the production of benzaldehyde with 40–50% selectivity by catalytic liquid phase air oxidation of toluene using a composite catalytic system which comprises the production of value added products benzaldehyde (40–50%), benzyl alcohol (5–10%) and benzoic acid in large proportions without any trace amounts of benzyl bromide maintaining transformation percentage <25% in the catalytic liquid phase air oxidation of toluene with continuous flow of air employing the significantly reduced quantities of salts of Fe, Co, Mn, Mo, Ni, as recyclable catalysts and cobalt bromide, sodium bromide, sodium chloride and zinc bromide as promoters as well as bromine source and low content of carboxylic acid such as acetic, propionic, benzoic acids as solvent in the range of 0.05 to 0.4 wt times with respect to toluene, at the temperatures of 60–130° C. and pressures in the range of 1–10 bar for a period of 0.5–1.5 hrs.

In the applicant's earlier patent EP 1088810 (U.S. application Ser. No. 09/414,473), the oxidation of toluene was carried out in the presence of 0.02, 0.0012, 0.04 gmol/L of cobalt acetate, manganese acetate and zinc bromide respectively. Conversion is <25% with 35–40% benzaldehyde and 50–55% benzoic acid selectivities. The novelty of the present method is using very low concentration of composite catalytic system consisting of cobalt acetate (0.01 gmol/L) as catalyst, manganese acetate (0.0008 gmol/L) as co-catalyst and zinc bromide (0.0147 gmol/L) or sodium bromide (0.032 gmol/L) as promoter. When compared with our earlier patent, the reduction of the bromine content by 8–32 times slows down corrosion of the reactor, a very important factor affecting economics of the project.

Another novelty of the present method is realisation of the high productivity benzaldehyde and benzyl alcohol in the air oxidation of toluene, with high turn over number. The use of manganese acetate as an initiator improved the conversion of toluene and yields of benzaldehyde and benzoic acid and thus recorded higher rate of productivity even at a low concentration of cobalt and high concentration of toluene. Even with the reduction of $Br^-$ content by 5–50 times as NaBr replaces $ZnBr_2$, it is observed that the conversion of the toluene and selectivity and yields towards benzaldehyde are not much affected. Low concentration of solvent, carboxylic acids in our reaction designed to release adequate free $Br^-$ which gives insitu free radical $Br^-$ on interaction with Mn (III) to the initiation of the reaction is employed to minimise the loss of expensive bromine in the form of volatile HBr and to minimize the corrosion problem. Use of mixture of NaBr/NaCl at lower ratio to accelerate the rate of the reaction and to afford higher selectivity towards benzaldehyde and benzyl alcohol is the ultimate choice, since it reduces the process cost. As the market demand for each product fluctuates, the dynamic system developed here as described is very important to enable to choose the required composition of $Br^-/Cl^-$ to obtain the desired product in excess quantities to meet the changing demands. A protocol for recovery and reuse of the composite catalyst is developed. Recycle and aging studies allowed to evolve the strategy for commercial production of benzaldehyde in high selectivities. UV-VIS studies identified mononuclear Co and Mn complexes as active species for selective oxidation of toluene to benzaldehyde. The process is environmentally safe since there is no effluent disposal problem as encountered in chlorination of toluene followed by oxidation.

BRIEF DESCRIPTION OF THE ACCOMPANYING DRAWING

FIG. 1 represents the results of the recycle experiments.

The present invention is further described with reference to the following examples which are given by way of illustration and therefore should not be construed to limit the scope of the present invention in any manner.

EXAMPLE 1

Buchi glass autoclave of 500 ml capacity equipped with a gas connecting tube, stirrer, temperature indicator and pressure gauge was deployed. The following materials were taken in the reaction vessel: 225 ml toluene, 75 ml of acetic acid, and 1.50 g of cobalt acetate, 0.09 g of manganese acetate.4 water salt, 2.7 g of zinc bromide. After flushing with air three times, the solution was heated slowly up to 110° C. while stirring the reaction mixture. After system attained a constant temperature of 110° C., it was pressurised with air to 10 bar with 2 L/min out flow. After 1:15 hrs, the reaction mixture was taken out. Gas chromatographic and titrimetric analysis on the product indicates conversion of 14.04% with selectivity of 42.3% benzaldehyde, 4.98% benzyl alcohol and 52.72% benzoic acid.

EXAMPLE 2

Buchi glass autoclave of 250 ml capacity equipped with a gas connecting tube, stirrer, temperature indicator and pressure gauge was deployed. The following materials were taken in the reaction vessel: 150 ml of toluene, 50 ml of acetic acid, and 0.5 g of cobalt acetate 4 water salt, 0.04 g of manganese acetate.4 water salt, 0.66 g of zinc bromide. After flushing with air three times, the solution was heated slowly up to 110° C. while stirring the reaction mixture. After system attained a constant temperature of 110° C., it was pressurised with air to 10 bar with 2 L/min out flow. After 1:15 hrs, the reaction mixture was taken out. Gas chromatographic and titrimetric analysis on the product indicates conversion of 15.78% with selectivity of 36.59% benzaldehyde, 6.04% benzyl alcohol and 57.37% benzoic acid.

EXAMPLE 3

Buchi glass autoclave of 250 ml capacity equipped with a gas connecting tube, stirrer, temperature indicator and pressure gauge was deployed. The following materials were taken in the reaction vessel: 150 ml of toluene, 50 ml of acetic acid, and 0.5 g of cobalt acetate.4 water salt, 0.04 g of manganese acetate.4 water salt, 0.106 g of sodium bromide, 0.314 g of sodium chloride. After flushing with air three times, the solution was heated slowly up to 110° C. while stirring the reaction mixture. After system attained a constant temperature of 110° C., it was pressurised with air to 10 bar with 2 L/min out flow. After 1:15 hrs, the reaction mixture was taken out. Gas chromatographic and titrimetric analysis on the product indicates conversion of 14.34% with selectivity of 42.61% benzaldehyde, 3.83% benzyl alcohol and 53.56% benzoic acid.

EXAMPLE 4

Buchi glass autoclave of 250 ml capacity equipped with a gas connecting tube, stirrer, temperature indicator and pressure gauge was deployed. The following materials were taken in the reaction vessel: 150 ml of toluene, 50 ml of acetic acid, and 0.5 g of cobalt acetate.4 water salt, 0.04 g of manganese acetate.4 water salt, 0.212 g of sodium bromide, 0.253 g of sodium chloride. After flushing with air three times, the solution was heated slowly up to 110° C. while stirring the reaction mixture. After the system attained a constant temperature of 110° C., it was pressurised with air to 10 bar with 2 L/min out flow. After 1:15 hrs, the reaction mixture was taken out. Gas chromatographic and titrimetric analysis on the product indicates conversion of 15.36% with selectivity of 37.71% benzaldehyde, 8.38% benzyl alcohol and 53.91% benzoic acid.

EXAMPLE 5

Buchi glass autoclave of 250 ml capacity equipped with a gas connecting tube, stirrer, temperature indicator and pressure gauge was deployed. The following materials were taken in the reaction vessel: 150 ml of toluene, 50 ml of acetic acid, and 0.5 g of cobalt acetate.4 water salt, 0.04 g of manganese acetate.4 water salt, 0.106 g of sodium bromide, 0.063 g of sodium chloride. After flushing with air three times, the solution was heated slowly up to 120° C. while stirring the reaction mixture. After system attained a constant temperature of 120° C., it was pressurised with air to 10 bar with 2 L/min out flow. After 1:00 hr, the reaction mixture was taken out. Gas chromatographic and titrimetric analysis on the product indicates conversion of 14.48% with selectivity of 36.26% benzaldehyde, 10.25% benzyl alcohol and 53.49% benzoic acid.

EXAMPLE 6

Buchi glass autoclave of 500 ml capacity equipped with a gas connecting tube, stirrer, temperature indicator and pressure gauge was deployed. The following materials were taken in the reaction vessel: 225 ml of toluene, 75 ml of acetic acid, and 1.5 g of cobalt acetate.4 water salt, 5.0 g of sodium bromide. After flushing with air three times, the solution was heated slowly up to 110° C. while stirring the reaction mixture. After system attained a constant temperature of 110° C., it was pressurised with air to 10 bar with 2 L/min out flow. After 2:00 hrs, the reaction mixture was taken out. Gas chromatographic and titrimetric analysis on the product indicates conversion of 14.79% with selectivity of 49.41% benzaldehyde, 5.19% benzyl alcohol and 45.40% benzoic acid.

EXAMPLE 7

Buchi glass autoclave of 250 ml capacity equipped with a gas connecting tube, stirrer, temperature indicator and pressure gauge was deployed. The following materials were taken in the reaction vessel: 150 ml of toluene, 50 ml of acetic acid, and 0.5 g of cobalt acetate.4 water salt, 0.04 g of manganese acetate.4 water salt, 0.66 g of sodium bromide. After flushing with air three times, the solution was heated slowly up to 110° C. while stirring the reaction mixture. After system attained a constant temperature of 110° C., it was pressurised with air to 10 bar with 2 L/min out flow. After 1:15 hrs, the reaction mixture was taken out. Gas chromatographic and titrimetric analysis on the product indicates conversion of 17.41% with selectivity of 40.60% benzaldehyde, 5.16% benzyl alcohol and 54.24% benzoic acid.

EXAMPLE 8

Buchi glass autoclave of 250 ml capacity equipped with a gas connecting tube, stirrer, temperature indicator and pressure gauge. The following materials were taken in the reaction vessel: 150 ml of toluene, 50 ml of acetic acid, and 0.5 g of cobalt acetate.4 water salt, 0.04 g of manganese acetate.4 water salt, 0.075 g of sodium bromide. After flushing with air three times, the solution was heated slowly upto 120° C. while stirring the reaction mixture. After system attained a constant temperature of 120° C., it was pressurised with air to 10 bar with 2 L/min out flow. After 1:00 hr, the reaction mixture was taken out. Gas chromatographic and titrimetric analysis on the product indicates conversion of 14.09% with selectivity of 38.80% benzaldehyde, 5.32% benzyl alcohol and 55.88% benzoic acid.

The reaction conditions, the concentration of the various salts and acids used, the percentage selectivity of the reaction to benzaldehyde, benzyl alcohol and benzoic acid in examples 1 to 8 are summarised in Table 1.

TABLE 1

Catalytic Liquid Phase Air Oxidation of Toluene[a]

| Ex. No. | Co.Ac (gmol/L) | Mn.Ac (gmol/L) | ZnBr$_2$ (gmol/L) | NaBr (gmol/L) | NaCl (gmol/L) | Temp (°C.) | Time (hr) | Conv (%) | Selectivity (%) | | |
|---|---|---|---|---|---|---|---|---|---|---|---|
| | | | | | | | | | BAld | BAlc | BAcid |
| 1[b] | 0.02 | 0.0012 | 0.04 | — | — | 110 | 1:15 | 14.04 | 42.3 | 4.98 | 52.72 |
| 2 | 0.01 | 0.0008 | 0.0147 | — | — | 110 | 1:15 | 15.78 | 36.59 | 6.04 | 57.37 |
| 3 | 0.01 | 0.0008 | — | 0.005 | 0.027 | 110 | 1:15 | 14.34 | 42.61 | 3.83 | 53.56 |
| 4 | 0.01 | 0.0008 | — | 0.01 | 0.022 | 110 | 1:15 | 15.36 | 37.71 | 8.38 | 53.91 |
| 5 | 0.01 | 0.0008 | — | 0.005 | 0.0054 | 120 | 1:00 | 14.48 | 36.26 | 10.25 | 53.49 |
| 6[b] | 0.02 | — | — | 0.16 | — | 110 | 2:00 | 14.79 | 49.41 | 5.19 | 45.40 |
| 7 | 0.01 | 0.0008 | — | 0.032 | — | 110 | 1:15 | 17.41 | 40.60 | 5.16 | 54.24 |
| 8 | 0.01 | 0.0008 | — | 0.0036 | — | 120 | 1:00 | 14.09 | 38.80 | 5.32 | 55.88 | a) Reaction Volume: 200 ml; Toluene: 64.32 w/v %; Pressure: 10 bar; Air flow: 2 L/min
b) Reaction Volume: 300 ml; Toluene: 64.32 w/v %; Pressure: 10 bar; Air flow: 2 L/min
Note:
BAld denotes benzaldehyde; BAlc denotes benzyl alcohol, and BAcid denotes benzoic acid

EXAMPLE 9

Catalyst Recycle Experiment

The reaction mixture of example 8 containing toluene, acetic acid, benzaldehyde, benzoic acid, benzyl alcohol and catalyst mixture was taken for recycle study. Toluene and acetic acid were removed by distillation from the reaction mixture and toluene was added to the product mixture residue to make it a homogeneous solution. Water was then added to the organic mixture and the catalyst was extracted into the aqueous layer, and organic and aqueous layers were separated. Organic layer was subjected to distillation to get toluene, benzaldehyde, benzyl alcohol and benzoic acid, and the aqueous layer was concentrated to get the catalyst composite mixture cake.

Buchi glass autoclave of 250 ml capacity equipped with a gas connecting tube, stirrer, temperature indicator and pressure gauge was deployed. The following materials were taken in the reaction vessel: 150 ml of toluene, 50 ml of acetic acid, recovered catalyst composite mixture cake containing cobalt acetate, manganese acetate, sodium bromide and make-up catalyst of 5% cobalt acetate, 5% manganese acetate and 100% sodium bromide (Fresh amounts of Co and Mn is charged to account for handling losses and sodium bromide for consumption). After flushing with air three times, the solution was heated slowly up to 120° C. while stirring the reaction mixture. After the system attained a constant temperature of 120° C., it was pressurised with air to 10 bar with 2 L/min out flow. After 1 hour, the reaction mixture was taken out. Gas chromatographic and titrimetric analysis on the product indicates conversion of 15.32% with selectivity of 40.16% benzaldehyde, 12.20% benzyl alcohol and 47.64% benzoic acid. Like this 10 recycles were conducted and the results were presented in FIG. 1.

The main advantages of the present invention are:
1. The process is a catalytic liquid phase reaction.
2. The selectivity for benzaldehyde obtained in this process is in the range of 40–50%.
3. The selectivity for benzyl alcohol obtained in this process is in the range of 5–10%.
4. Low concentration of catalyst, co-catalyst and promoter is used.
5. The temperatures and pressures employed in the reaction are moderate.
6. The residence time in the reactor is short.
7. Acetic acid is used as the solvent and the amount used is in the range of 0.05 to 0.4 wt times with respect to toluene.
8. An ecofriendly process for the production of benzaldehyde without the formation of benzyl bromide was developed.
9. Benzaldehyde produced is free from chlorine and can be used over a wide range of applications.
10. High turn over number 900–1200 is realised for the first time.
11. The catalytic system is recyclable with almost consistent activity and selectivity.
12. Employment of the low concentration catalytic system slows down corrosion on the reactor, a very important factor affecting economics of the project.
13. The present process is environmentally safe since there is no effluent disposal problem.
14. The process is economical.

What is claimed is:

1. An improved process for preparing benzaldehyde with a 40–50% selectivity and a conversion percentage of 25% by a catalytic liquid phase oxidation of toluene by using a composite catalytic system along with production of value added products benzyl alcohol and benzoic acid, said process comprising: conducting a catalytic liquid phase air oxidation of toluene with a continuous flow of air in the presence of a salt of Iron, Cobalt, Manganese, Molybdenum or Nickel as a recyclable catalyst, manganese or copper salts as a recyclable co-catalyst, and cobalt bromide, sodium bromide, sodium chloride or zinc bromide as a promoter, and 0.05 to 0.4% by wt. of a carboxylic acid at a temperature of 60–130° C. and a pressure of 1–10 bar for a period of 0.5–1.5 hrs,
wherein the concentration of the recyclable catalyst with respect to toluene is in the range of 0.01–0.027 gmol/L,
the concentration of the recyclable co-catalyst with respect to toluene is in the range of 0.001–0.002 gmol/L,
the concentration of the promoter with respect to the toluene is in the range of 0.001–0.215 gmol/L, and
the turn over number is in the range of 900–1200.

2. A process as claimed in claim 1, wherein the conversion percentage is 15–25%.

3. A process as claimed in claim 1, wherein the selectivity to benzyl alcohol is 5–10%.

4. A process as claimed in claim 1, wherein the carboxylic acid is selected from the group consisting of acetic acid, propionic acid and benzoic acids.

5. A process as claimed in claim 4, wherein the carboxylic acid is acetic acid.

6. A process as claimed in claim 1, wherein the catalyst contains cobalt, molybdenum or iron.

7. A process as claimed in claim 1, wherein the catalyst and co-catalyst are organic acid salts.

8. A process as claimed in claim 1, wherein the promoter is cobalt, sodium or zinc bromide.

9. An improved process for preparing benzaldehyde with a 40–50% selectivity and a conversion percentage of 25% or less, by a catalytic liquid phase oxidation of toluene by using a composite catalytic system along with production of value added products benzyl alcohol and benzoic acid, without any trace amounts of benzyl bromide, said process comprising: conducting a catalytic liquid phase air oxidation of toluene with a continuous flow of air in the presence of a salt of Iron, Cobalt, Manganese, Molybdenum or Nickel as a recyclable catalyst, manganese or copper salts as a recyclable co-catalyst, and cobalt bromide, sodium bromide, sodium chloride or zinc bromide as a promoter, and 0.05 to 0.4% by wt. of a carboxylic acid at a temperature of 60–130° C. and a pressure of 1–10 bar for a period of 0.5–1.5 hrs.

wherein an admixture of Cl⁻ to Br⁻ ions available from the co-catalyst enhances the rate of air oxidation of toluene and ensures that the product mixture is devoid of benzyl bromide.

10. A process as claimed in claim 1, wherein the a plurality of recycle reactions are conducted with the recovered catalyst, wherein each of the plurality of recycle reactions provides near identical conversions and selectivities obtained with an addition of an amount of the promoter or a bromide on each recycle.

11. A process as claimed in claim 1, wherein the concentration of the promoter is effective to reduce corrosion of the reactor in comparison with a concentration of promoter having a greater bromine content.

12. An improved process for preparing benzaldehyde with a 40–50% selectivity and a conversion percentage of 25% or less, by a catalytic liquid phase oxidation of toluene by using a composite catalytic system along with production of value added products benzyl alcohol and benzoic acid, without any trace amounts of benzyl bromide, said process comprising: conducting a catalytic liquid phase air oxidation of toluene with a continuous flow of air in the presence of a salt of Iron, Cobalt, Manganese, Molybdenum or Nickel as a recyclable catalyst, manganese or copper salts as a recyclable co-catalyst, and cobalt bromide, sodium bromide, sodium chloride or zinc bromide as a promoter, and 0.05 to 0.4% by wt. of a carboxylic acid at a temperature of 60–130° C. and a pressure of 1–10 bar for a period of 0.5–1.5 hrs, wherein the catalyst and co-catalyst are recycled for 10 cycles and provide almost consistent activity and selectivity.

13. A process as claimed in claim 1, wherein no benzyl bromide is formed as a by-product.

14. A process as claimed in claim 1, wherein the benzaldehyde produced is chlorine free.

15. A process as claimed in claim 7, wherein each organic acid salt is selected from the group consisting of formic acid salts, acetic acid salts and propionic acid salts.

* * * * *